United States Patent
Carnahan et al.

(10) Patent No.: US 6,868,715 B1
(45) Date of Patent: Mar. 22, 2005

(54) METHOD AND APPARATUS FOR RAPID DETERMINATION OF POLYMER MOLECULAR WEIGHT

(75) Inventors: James Claude Carnahan, Niskayuna, NY (US); Paul Edward Gundlach, Scotia, NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/665,767

(22) Filed: Sep. 20, 2000

(51) Int. Cl.$^7$ .......................... G01N 9/00; B01D 15/08
(52) U.S. Cl. ........................... 73/64.54; 210/659
(58) Field of Search .................. 73/64.54; 356/335, 356/336, 344; 210/656, 659

(56) References Cited

U.S. PATENT DOCUMENTS

| | | | |
|---|---|---|---|
| 3,522,725 A | | 8/1970 | Waters |
| 4,178,103 A | | 12/1979 | Wallace .................. 356/336 |
| 4,616,927 A | | 10/1986 | Phillips et al. .............. 356/338 |
| 5,129,723 A | * | 7/1992 | Howie et al. ............... 356/336 |
| 5,214,073 A | * | 5/1993 | Fukawa et al. .............. 521/60 |
| 5,214,183 A | * | 5/1993 | Fyvie et al. ............... 558/268 |
| 5,414,144 A | * | 5/1995 | Watanabe et al. ........... 568/670 |
| 5,528,366 A | | 6/1996 | Shortt |
| 5,530,540 A | | 6/1996 | Wyatt et al. ................ 356/246 |
| 5,840,256 A | | 11/1998 | Demers et al. ............. 422/102 |
| 5,846,396 A | | 12/1998 | Zanzucchi et al. .......... 204/601 |
| 5,854,084 A | * | 12/1998 | Drukier et al. ............. 436/541 |
| 5,854,684 A | | 12/1998 | Stabile et al. .............. 356/440 |
| 5,938,932 A | * | 8/1999 | Connelly et al. ........... 210/659 |
| 5,985,356 A | | 11/1999 | Schultz et al. ................. 427/8 |
| 6,045,671 A | | 4/2000 | Wu et al. .................... 204/298 |
| 6,175,409 B1 | * | 1/2001 | Nielsen et al. .............. 356/337 |
| 6,176,952 B1 | * | 1/2001 | Maugans et al. ........... 156/73.1 |
| 6,235,844 B1 | * | 5/2001 | Dadgar et al. .............. 525/184 |
| 6,260,407 B1 | * | 7/2001 | Petro et al. ............. 210/198.2 |
| 6,265,226 B1 | * | 7/2001 | Petro et al. ................. 422/100 |
| 6,294,388 B1 | * | 9/2001 | Petro ................... 435/DIG. 29 |
| RE37,400 E | * | 10/2001 | Canich ........................ 556/11 |
| 6,296,771 B1 | * | 10/2001 | Miroslav et al. ............ 210/656 |
| 6,303,688 B1 | * | 10/2001 | Schauder ..................... 525/63 |
| 6,329,450 B1 | * | 12/2001 | Ogoe et al. ................... 524/35 |
| 6,344,172 B1 | * | 2/2002 | Afeyan et al. .............. 210/656 |
| 6,413,431 B1 | * | 7/2002 | Abedi ........................ 210/656 |
| 6,627,453 B1 | * | 9/2003 | Hindsgaul et al. .......... 436/161 |

OTHER PUBLICATIONS

Allcock, H. R. and Lampe, F. W. Contemporary Polymer Chemistry, Prentice Hall, $2^{nd}$ edition, 1990 (no month), p. 29.*

U.S. provisional application No. 60/157,338, filed on Oct. 1,1999.*

(List continued on next page.)

*Primary Examiner*—Michael Cygan
(74) *Attorney, Agent, or Firm*—Andrew J. Caruso; Philip D. Freedman (57) ABSTRACT

A rapid analysis method for the determination of polymer average molecular weight separates the polymer's high molecular weight fraction and determines its average molecular weight using a molar mass detector and a concentration detector. The method avoids time consuming sample preparation, allows for separation of interfering low molecular weight components, and is suitable for automation.

34 Claims, 3 Drawing Sheets

OTHER PUBLICATIONS

Knobloch, James E. et al. Analytical Biochemistry vol. 245, Jun. 1997, pp. 231–241.*

BH Zimm, *J. Chem. Phys.*, "Apparatus and Methods for Measurement and Interpretation of the Angular Variation of Light Scattering; Preliminary Results on Polystyrene Solutions", vol. 16, pp. 1099–1116 (1948), Dec. 1948.

PJ Wyatt, *Analytica Chimica Acta*, "Light Scattering and The Absolute Characterization of Macromolecules", vol. 272, pp. 1–40 (1993), Jan. 1993.

TH Mourey, SM Miller and ST Balke, *Journal of Liquid Chromatography*, "Size Exclusion Chromatography Assessment Utilizing Coupled Molecular Weight Detectors", vol. 13, pp. 435–452 (1990), Dec. 1970.

WW Yau and SW Rementer, *Journal of Liquid Chromatography*, "Polymer Characterization by SEC–Viscometry: Molecular Weight, Size and Intrinsic Viscosity Distribution", vol. 13, pp. 627–675–452 (1990), Feb. 1990.

* cited by examiner

Fast GPC 2.0 ml/min

METHOD AND APPARATUS FOR RAPID DETERMINATION OF POLYMER MOLECULAR WEIGHT

BACKGROUND OF THE INVENTION

The present invention relates to analysis of polymer resins. In particular, the invention relates to determination of polymer molecular weight.

Early methods for the determination of polymer molecular weight relied on chromatographic separation and comparison to polymer standards with narrow, known molecular weight distributions. These methods were very slow and subject to large experimental errors.

The use of light scattering methods for polymer characterization, in pioneered by Zimm (see, for example, *Journal of Chemical Physics*, volume 16, number 12, pages 1099–1116 (1948)), offered the advantage of absolute determination of molar mass. Light scattering methods have been used in static and flow analysis systems for characterization of polymer solutions without separation, but these measurements are unsuitable for analysis of polymerization reaction mixtures because the presence of low molecular weight reactants, products, and catalysts interferes with the accurate determination of average molecular weight for the polymeric component of the reaction mixture.

When paired with size exclusion chromatography and a concentration detection method such as differential refractive index, light scattering detection enables precise characterization of the molecular weight distribution of polydisperse polymer samples. See, for example, P. J. Wyatt, *Analytica Chimica Acta*, volume 272, pages 1–40 (1993). However, known methods combining chromatographic separation and light-scattering detection require several minutes for analysis of each sample.

When modern combinatorial methods are used to screen polymerization reaction conditions or catalyst materials, there is often a desire to determine the average molecular weight of the product polymer. However, the large number of samples generated by combinatorial methods can easily overwhelm the traditional analyses described above.

There is therefore a need for an analytical method that enables rapid molecular weight determination of polymer resins, is free from interferences by small molecules, and is easily automated.

BRIEF SUMMARY OF THE INVENTION

Rapid determination of the average molecular weight of aromatic polycarbonate resins is provided by a method comprising:

injecting a known volume of an analytical sample comprising a polymer into a flow analysis system comprising a chromatographic column, a concentration detector, and a molar mass detector;

effecting a minimally dispersive separation of the analytical sample with the chromatographic column to yield a high molecular weight fraction;

determining the polymer concentration in the high molecular weight fraction using the concentration detector;

determining the molar mass in the high molecular weight fraction using the molar mass detector; and deriving an average molecular weight from the polymer concentration and the molar mass;

wherein the total analysis time is not greater than about 5 minutes per sample.

BRIEF DESCRIPTION OF THE DRAWINGS

FIG. 4 shows chromatograms for light scattering (A) and differential refractive index (B) detection of the high molecular weight fraction of a polycarbonate polymerization reaction mixture.

DETAILED DESCRIPTION OF THE INVENTION

Rapid determination of polymer average molecular weight is provided by a method comprising:

injecting a known volume of an analytical sample comprising a polymer into a flow analysis system comprising a chromatographic column, a concentration detector, and a molar mass detector;

effecting a minimally dispersive separation of the analytical sample with the chromatographic column to yield a high molecular weight fraction;

determining the polymer concentration in the high molecular weight fraction using the concentration detector;

determining the molar mass in the high molecular weight fraction using the molar mass detector; and deriving an average molecular weight from the polymer concentration and the molar mass;

wherein the total analysis time is not greater than about 5 minutes per sample.

The method comprises injecting a known volume of an analytical sample comprising a polymer in solution. The polymer may be organic or inorganic, biological or non-biological in origin. In a preferred embodiment, the polymer is a non-biological organic polymer. In a more preferred embodiment, the polymer is a polycarbonate, polyester, polyamide or polyimide. In a highly preferred embodiment, the polymer comprises an aromatic polycarbonate or a polyester.

Aromatic polycarbonates are a well-known class of polymers and their preparation is described in, among many others, U.S. Pat. No. 3,028,365 to Schnell et al. U.S. Pat. No. 3,334,154 to Kim, U.S. Pat. No. 3,989,672 to Vestergaard, U.S. Pat. No. 4,131,575 to Adelmann et al., and U.S. Pat. No. 5,606,008 to Sakashita et al.; and Japanese Unexamined Patent Publications JP 2000-063507-A, JP 11-005837-A and JP11-158261-A. Aromatic polycarbonates comprise repeating units of the formula wherein $A^1$ is a divalent aromatic radical derived from a dihydric phenol. The dihydric phenol employed to provide such aromatic polycarbonate polymers is a mononuclear or polynuclear aromatic compound containing as functional groups two hydroxyl radicals, each of which is attached directly to a carbon atom of an aromatic nucleus. Typical dihydric phenols include 2,2-bis-(4-hydroxyphenyl)propane (also known as bisphenol A or BPA); hydroquinone; resorcinol; 2,2-bis-(4-hydroxyphenyl)pentane; 2,4'-dihydroxydiphenylmethane; bis-(2-hydroxyphenyl) methane; bis-(4-hydroxyphenyl)methane; bis-(4-hydroxy-5-nitrophenyl)methane; 1,1-bis-(4-hydroxyphenyl)ethane; 3,3-bis-(4-hydroxyphenyl)pentane; 2,2'-dihydroxydiphenyl; 2,6dihydroxynapthylene; bis-(4-hydroxyphenyl)sulfone; 2,2'-dihydroxydiphenylsulfone; 4,4'-dihydroxydiphenylether; 4,4'-dihydroxy-2,5-diethoxydiphenylether; and 1,1-bis(3-methyl-4-hydroxyphenyl)cyclohexane. A variety of additional dihydric phenols are disclosed in U.S. Pat. No. 2,999,835 to Goldberg. It is possible to employ two or more different dihydric phenols, or a dihydric phenol in combination with a glycol, a hydroxy or acid-terminated polyester, or a dibasic acid in order to prepare a carbonate copolymer. Such carbonate copolymers are expressly encompassed by the term "aromatic polycarbonates" as used hereinafter. Preferred dihydric phenols include bis-(2-hydroxyphenyl)methane, 1,1-bis-(4-hydroxyphenyl)ethane, 2,2-bis-4-hydroxyphenyl) propane, 2,2-bis-(4-hydroxyphenyl)pentane, and 1,1-bis(3-methyl-4-hydroxyphenyl)cyclohexane. A highly preferred dihydric phenol is 2,2-bis-(4-hydroxyphenyl)propane.

Polyesters suitable for analysis include those comprising repeating units of the formula wherein each R is independently a divalent aliphatic, alicyclic, or aromatic hydrocarbon or polyoxyalkylene radical; and each $A^2$ is independently a divalent aliphatic, alicyclic, or aromatic radical. The R radical may be, for example, a $C_{2-10}$ alkylene radical, a $C_{6-10}$ alicyclic radical, a $C_{6-20}$ aromatic radical, or a polyoxyalkylene radical in which the alkylene groups contain about 2–6 and most often 2 or 4 carbon atoms. Specific R radicals may be those derived from diols including ethylene glycol, propylene glycols, butylene glycols, cyclohexanedimethanol, cyclobutanedimethanol, or any of the dihydric phenols described above in relation to polycarbonates. The $A^2$ radical may be derived from terephthalic acid, isophthalic acid, naphthalene dicarboxylic acid, cyclohexane-1,4-dicarboxylic acid, cyclohexane-1,3-dicarboxylic acid, and aliphatic dicarboxylic acids such as oxalic acid, maleic acid, succinic acid, glutaric acid, adipic acid, pivalic acid, and longer chain di-acids. The $A^2$ radical is most often p-phenylene or m-phenylene, or a mixture thereof. Specific polyesters include the poly(alkylene terephthalates), the poly(alkylene isophthalates), the poly(alkylene napthalates), and the polyarylates. Such polyesters are described in, for example, U.S. Pat. Nos. 2,465,319; 2,720,502; 2,727,881; 2,822,348; 3,047,539; 3,671,487; 3,953,394; and 4,128,526.

In a preferred embodiment, the analytical sample comprises a polymerization reaction mixture. Thus, the sample may comprise, for example, reactants (e.g., monomers), catalysts, pH buffers, and non-polymeric products, in addition to oligomeric and polymeric products of polymerization. When the polymer comprises an aromatic polycarbonate, the reaction mixture may comprise, for example, the reactants diphenyl carbonate and bisphenol A, the product phenol, and a catalyst, in addition to polycarbonate oligomers and polymers.

The analytical sample may be prepared by dissolving the polymer in a suitable solvent. Choice of a suitable solvent will, of course, depend, among other factors, on the chemical composition of the polymer, its molecular weight, and the desired concentration of the resulting solution. For most polymers, suitable solvents are well known in the art. For other polymers, suitable solvents may be determined with minimal experimentation, as, for example, by surveying polymer solubility in a limited set of solvents or solvent mixtures spanning a range of solvation parameters. When the polymer comprises aromatic polycarbonate, suitable solvents include benzene, toluene, xylene, chloroform, tetrahydrofliran, chlorobenzene, dichlorobenzene, trichlorobenzene, methylene chloride, trichloroethylene, dichloroethane, methyl acetate, ethyl acetate, and mixtures comprising at least one of the foregoing solvents. Preferred solvents for aromatic polycarbonate include chloroform, tetrahydrofuran, benzene, toluene, xylene, dichloromethane, and mixtures comprising at least one of the foregoing solvents. When the polymer comprises polyester, preferred solvents include chloroform, methylene chloride, trichloroethylene, dichloroethane, hexafluoroisopropanol, and mixtures comprising at least one of the foregoing solvents.

In a preferred embodiment, a plurality of analytical samples comprising polymer are provided. In a highly preferred embodiment, a plurality of analytical samples are provided, having been prepared from at least one combinatorial sample array. Specifically, the at least one sample array comprises a plurality of spatially differentiated sites, each site comprising a polymer resin. Each site may represent, for example, a distinct set of polymerization reaction conditions in one well of a 96-, 384-, or 1536-well plate. Such multiwell plates are well known and they may be obtained commercially or prepared by published methods. The exact number of analytical samples constituting a plurality may vary widely, from two to about one million or more. For example, U.S. Pat. No. 5,854,684 to Stabile et al. describes analytical matrices comprising at least one million samples arranged in a density of at least about 10 sites per square centimeter, and U.S. Pat. No. 5,840,256 to Demers et al. provides details for a 7.25 square inch analytical matrix comprising 99,856 samples. Microscale reaction vessels and methods of delivering reagents to them are described in, for example, U.S. Pat. No. 5,846,396 to Zanzucchi et al., U.S. Pat. No. 5,985,356 to Schultz et al., and U.S. Pat. 6,045,671 to Wu et al. An analytical sample corresponding to each spatially differentiated site may be prepared by adding a suitable solvent and dissolving some or all of the polymer resin. One of the advantages of the method is that the precise concentration of the polymer in the analytical sample is determined by the analysis and need not be known at the time of sample preparation. The resulting analytical solution comprising polymer may be analyzed immediately. Alternatively, the analytical solution may be stored for analysis at a later time, which may be useful, for example, when the time required to prepare an analytical sample from a given site exceeds the time required to analyze the sample.

The method comprises injecting a known volume of the analytical sample into a flow analysis system comprising a chromatographic column, a concentration detector, and a molar mass detector. The basic architecture of a flow analysis system is shown, for example in U.S. Pat. No. 3,522,725 to J. L. Waters, which describes a system comprising a solvent pump, a sample injector, a chromatographic column, and a detector. The concentration detector and the molar mass detector are described below. In the present method, a known volume of the analytical sample comprising polymer is withdrawn for analysis and injected into the system using a sample injector. Sample injectors are commercially available, and presently preferred injectors include the WISP Model 712 autosampler available from Waters Associates, and the Hewlett Packard model 1050 autoinjector available from Hewlett Packard (now Agilent Technologies). The injected sample travels through a minimum length of chromatographic tubing to at least one chromatographic column, which effects a minimally dispersive separation. A minimally dispersive separation is one that rapidly but substantially separates a high molecular weight fraction (HMWF) from a low molecular weight fraction (LMWF). The high molecular weight fraction is defined herein as comprising all oligomeric and polymeric products having at least two monomer units of at least one monomer. For example, the high molecular weight fraction of a sample comprising polycarbonate would comprise polycarbonate oligomers and polymers comprising at least two bisphenol A units. The low molecular weight fraction comprises, at minimum, any monomers from which the polymer is derived, but preferably also comprises other reagents, catalysts, and products having molecular weights lower than the molecular weights of the oligomeric and polymeric products. For example, the low molecular weight fraction of a sample comprising polycarbonate derived from bisphenol A and diphenyl carbonate would comprise bisphenol A, diphenyl carbonate, phenol and trace amounts of catalyst. A substantial separation of HMWF and LMWF is defined herein as elution of at least about 99 weight percent of the HMWF over a range of elution times that does not overlap with elution of more than about 1 weight percent of the LMWF, where the frame of reference for elution time is the concentration detector or the molar mass detector. In practical chromatographic terms, it is preferred that a baseline separation of the HMWF and the LMWF be achieved at the concentration detector and the molar mass detector. In order to enable the fastest possible analysis time, it is preferred that the minimally dispersive separation create the least possible dispersion of the HMWF while maintaining its separation from the LMWF. For example, the minimally dispersive separation may yield a high molecular weight fraction having a baseline peak width less than about 30 seconds, preferably less than about 20 seconds, more preferably less than about 10 seconds, at the molar mass detector or the concentration detector or both. Alternatively, the minimally dispersive separation may yield a high molecular weight fraction having a peak width at half height less than about 10 seconds, preferably less than about 5 seconds, more preferably less than about 3 seconds at the molar mass detector or the concentration detector or both. It is expressly contemplated to use two or more chromatographic columns in series to achieve the minimally dispersive separation. For example, a first column could effect a separation based on polarity, and a second column could effect a separation based on molecular size.

The chromatographic column may utilize any separation technique suitable to effect the above described minimally dispersive separation. Suitable techniques include size exclusion chromatography (also known as gel permeation chromatography), reverse phase chromatography, sedimentation field flow fractionation, thermal field flow fractionation, capillary electrophoresis, and ion exchange chromatography. Size exclusion chromatographic columns are presently preferred and are commercially available as, for example, the 50×7 millimeter 100 Angstrom column available from Polymer Laboratories as part number 1110-1520.

The method further comprises determining the polymer concentration in the high molecular weight fraction using at least one concentration detector. The concentration detector utilizes one or more detection methods including infrared absorption spectroscopy, ultraviolet absorption spectroscopy, differential refractive index detection, fluorescence detection and ultrasonic detection. Sample destructive detectors such as the evaporative light scattering detector (Varex Corp. and others) may also be used but must be placed downstream of the molar mass detector or in a split stream. The use of differential refractive index detection is presently preferred. Differential refractive index detectors are commercially available as, for example, the HP 1047A detector from Hewlett Packard (now Agilent Technologies). Raw data from the in-line determination of polymer concentration correspond to a series of (x,y) points where x is the elapsed time since injection and y is the detector response. A plot of these points forms a chromatogram, and a baseline-to-baseline integration of the peak of interest yields an area that is directly proportional to the polymer concentration. In addition, the signal intensity at any point in time is proportional to the instantaneous concentration at that time. In practice, analytical samples containing known polymer concentrations may be analyzed in a calibration experiment to derive the linear function that relates peak area or signal intensity to polymer concentration.

The method further comprises determining the molar mass in the high molecular weight fraction using one or more molar mass detectors. Molar mass detection may be accomplished by a variety of methods, including light scattering, such as low angle light scattering and multiangle light scattering; and viscometry. In addition, combinations of light scattering and viscometry detection can afford confirmatory benefits in determination of molecular weight. The use of multiangle light scattering is presently preferred, although commercial 90° light scattering detectors such as those from Viscotek Corp. can also be used. Multiangle light scattering detectors are commercially available as, for example, the DAWN® DSP multiangle light scattering detector from Wyatt Technologies.

Figure 1:
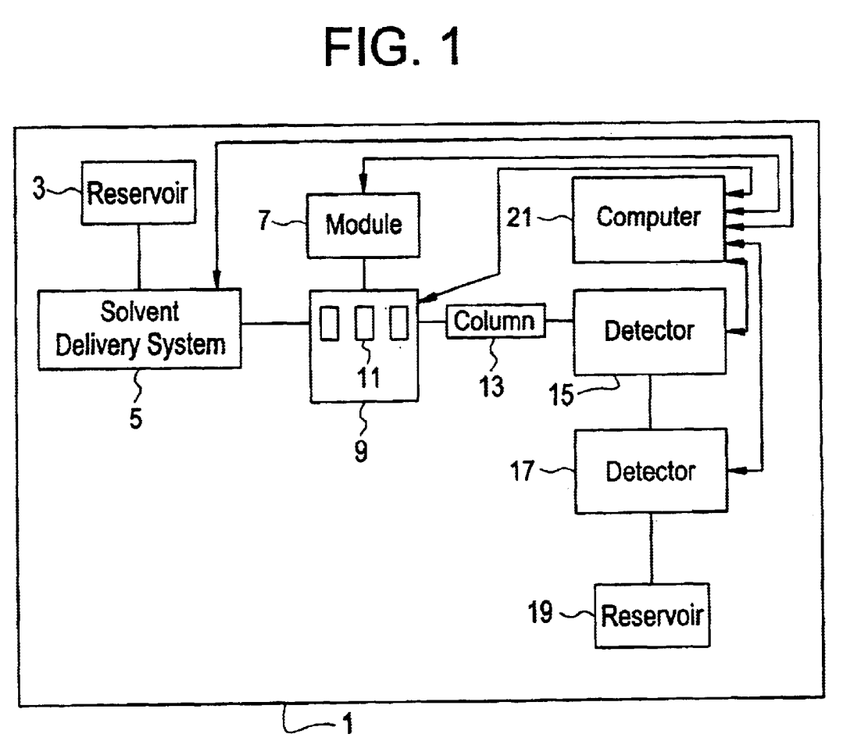
FIG. 1 is a block diagram of a system for determining polymer molecular weight; the concentration and molar mass detectors are linked in series.
Figure 2:
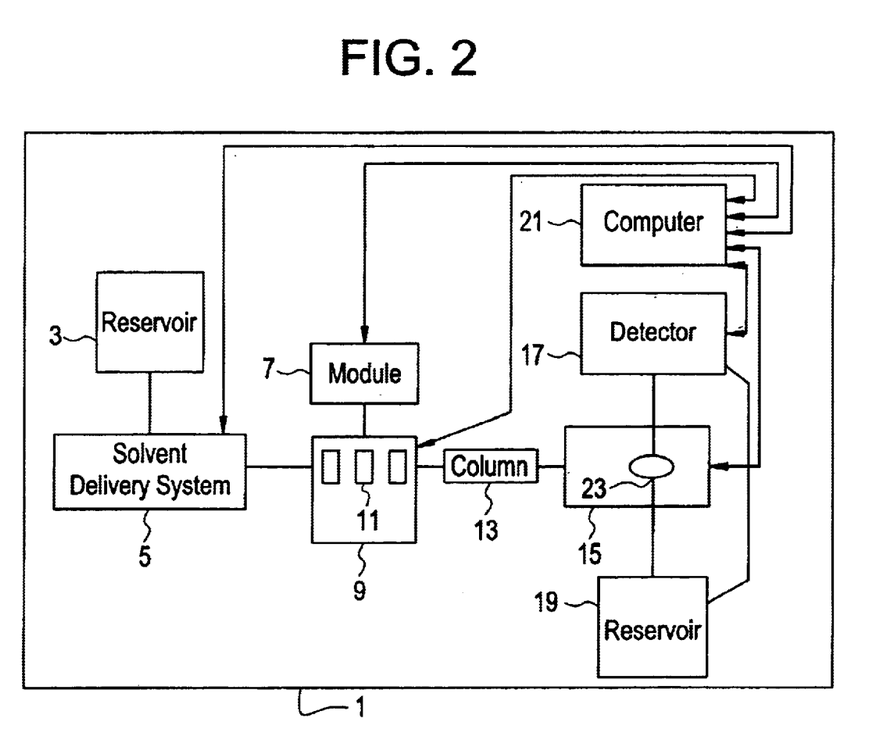
FIG. 2 is a block diagram of a system for determining polymer molecular weight; the molar mass detector is off-line from the main sample flow.

The determinations of polymer concentration and molar mass may be conducted sequentially in either order. Both determinations may be conducted on-line, i.e., as the sample is flowing in a single path with pumped solvent from the chromatographic column through both detectors to a waste reservoir. This configuration is shown in FIG. 1. Alternatively, the molar mass determination may be conducted off-line after the concentration determination by diverting the high molecular weight fraction to a molar mass detector that has a cell capable of containing and effecting rapid mixing of the entire HMWF that is separable from the main flow of pumped solvent. The off-line embodiment permits more accurate determination of the average molecular weight and simplifies the calculation of average molecular weight. This is then equivalent to determination with zero dispersion or separation of the polymer but permits elimination of interfering low molecular weight substances. This configuration is shown in FIG. 2.

The method further comprises deriving an average molecular weight from the polymer concentration and the molar mass. The average molecular weight may be either a weight average molecular weight or a number average molecular weight. Methods for deriving average molecular weight from molar mass and concentration detection data are well known in the art and reviewed in, for example, P. J. Wyatt, *Analytica Chimica Acta*, volume 272, pages 1–40 (1993). The derivation of an average molecular weight may include an estimation of the precision associated with the derivation. A method for such a precision determination is described in U.S. Pat. No. 5,528,366 to Shortt.

A key advantage of the method is its speed. The total analysis time per sample, measured from the injection of one sample to the injection of the following sample, is not greater than about five minutes, preferably not greater than about three minutes, more preferably not greater than about one minute, yet more preferably not greater than about 40 seconds.

In a preferred embodiment, the method is automated so that preparation and analysis of a plurality of analytical samples comprising polymer are prepared and analyzed without human intervention. Such automated methods may use a solvent preparation module for robotic preparation of solvent-containing analytical samples from a plurality of solid polymer samples, such as samples in a combinatorial library. Methods and equipment, including commercially available equipment, for automating sample preparation and analysis are known to those of ordinary skill in the art. Solvent addition to polymers in array plates may be made in a single action via equipment such as Quadra 96 Model 230 automatic pipettors or serially by any of a number of commercially available dosing robots and pipettors. Manufacturers include, for example, Gilson, Hamilton, Zinnser, and Packard Instruments. Such automated methods for sample preparation and analysis may include the use of variable temperatures, pressures and atmospheres.

In addition to the method described above, the invention encompasses a system for rapidly determining the average molecular weight of a polymer. FIG. 1 shows a block diagram for an analytical system 1 for determining molecular weight in samples comprising polymer. The system comprises a solvent reservoir 3, a solvent delivery system 5 for providing a flow of solvent that carries the sample through the system 1; an (optional) sample preparation module 7 for preparing analytical sample solutions from polymer samples; an autoinjector 9 for injecting a known portion of each analytical sample 11 into the system; a chromatographic column 13 for separating the high molecular weight fraction of the injected portion of analytical sample 11; a concentration detector 15 for determining the concentration of polymer in the high molecular weight fraction of the analytical sample 11; a molar mass detector 17 for determining the molar mass of the high molecular weight fraction of the analytical sample 11; a waste reservoir 19; and an (optional) computer 21 for deriving an average molecular weight from the polymer concentration and molar mass, and, optionally, for responsively controlling one or more of the solvent delivery system 5, the sample preparation module 7, the autoinjector 9, the concentration detector 15, and the molar mass detector 17. Although this embodiment is not shown, the molar mass detector 17 may precede the concentration detector 15. In a preferred embodiment, the system performs automated analyses of a plurality of analytical samples.

An alternative embodiment is shown in FIG. 2. The components and configuration are the same as shown and described for FIG. 1, except that the molar mass detector 17 is off-line from the main flow of solvent through the system, and a valve 23 controls selective diversion of the high molecular weight fraction to the molar mass detector 17 and subsequently to waste after completion of the analysis.

The invention is further illustrated by the following non-limiting example.

EXAMPLE

Figure 3:
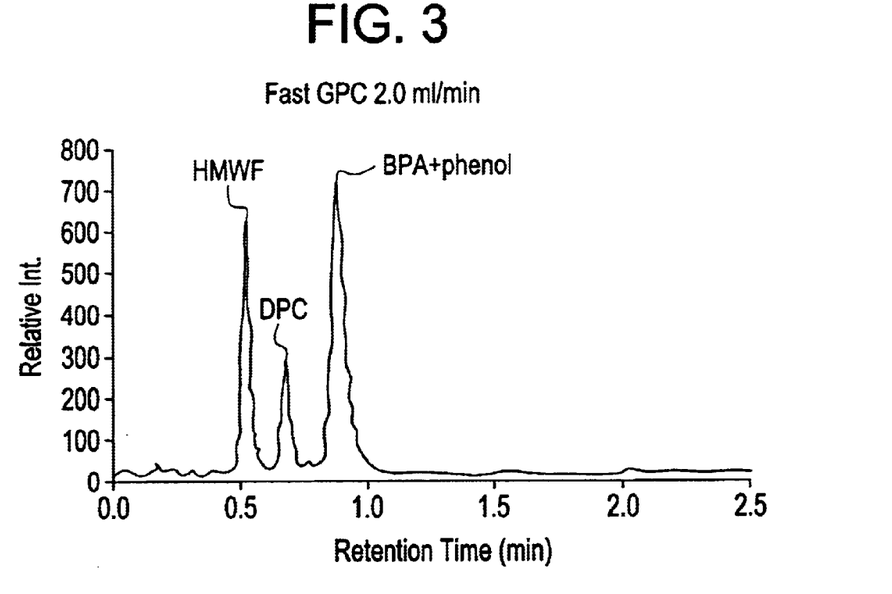
FIG. 3 is a chromatogram showing rapid separation of a polycarbonate high molecular weight fraction (HMWF) from reactant diphenyl carbonate (DPC), reactant bisphenol A (BPA), and product phenol in a polycarbonate polymerization reaction mixture; ultraviolet detection was employed.
Figure 4A:
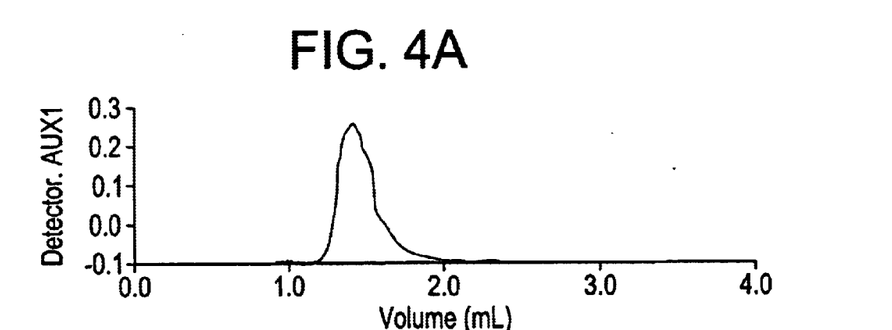
Figure 4B:
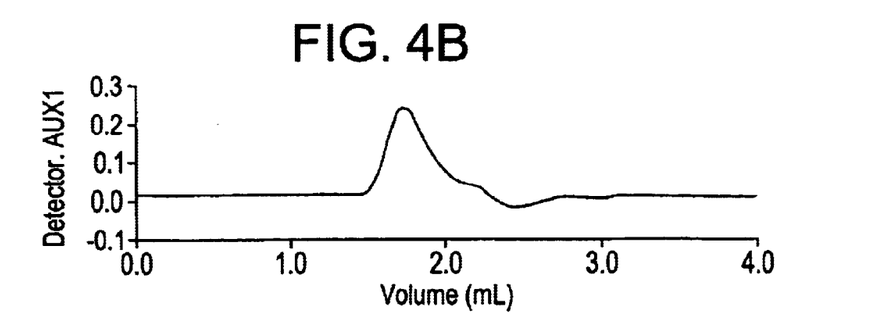

This example demonstrates the rapid determination of weight average molecular weights for a variety of polycarbonate samples. A Waters Associates Model 590 pump, a Waters Associates WISP Model 712 autosampler and a 50×7 millimeter 100 Angstrom column from Polymer Laboratories Part number 1110-1520) were connected in series to a Waters Assoc. Model 441 Absorbance detector, a Wyatt Technology Corporation DAWN® DSP multi-angle light scattering photometer and an HP 1047A Differential Refractive Index (DRI) detector. This arrangement corresponds to the configuration of FIG. 1. The flow rate of the chloroform solvent was 2.0 milliliters per minute, giving a total analysis time of less than one minute. The results of analysis of polycarbonate standards and of resins prepared by melt polymerization of bisphenol A and diphenylcarbonate gave the results in the Table, below. Each sample was analyzed at least twice at 30, 50 and 200 microliter ($\mu$L) injection volumes, and a weight average molecular weight ($M_w$) was calculated for each run based on data from the concentration and molar mass detectors. In the four cases in which a sample was analyzed three times at the same injection volume, a relative standard deviation (RSD) was calculated. An example of the fast chromatography utilizing the UV detector as concentration detector is shown in FIG. 3. This chromatogram shows that the high molecular weight fraction (HMWF) has finished eluting after about 0.6 minutes, indicating that a time between injections of about 0.6 minutes is feasible if overlapping injections are employed. Example of light scattering (A) and differential refractive index (B) traces collected at a slower flow rate are shown in FIG. 4.

TABLE

| Sample Number | Injection Volume ($\mu$L) | $M_w$ (DRI) | RSD (DRI) |
|---|---|---|---|
| 1 | 30 | 19200 | |
| | 30 | 19170 | |
| | 50 | 18520 | |
| | 50 | 19000 | |
| | 200 | 17100 | 0.46% |
| | 200 | 17190 | |
| | 200 | 17000 | |
| 2 | 30 | 11190 | |
| | 30 | 11360 | |
| | 50 | 10950 | |
| | 50 | 11060 | |
| | 200 | 10150 | 0.5% |
| | 200 | 10280 | |
| | 200 | 10220 | |
| 3 | 30 | 33980 | |
| | 30 | 33870 | |
| | 50 | 32350 | |
| | 50 | 32970 | |
| | 200 | 30160 | |
| | 200 | 29850 | |

This example show that determinations of average molecular weight can be conducted for a plurality of samples with a total analysis time of about 36 seconds per sample. The repeatability of the determination over a range of injection volumes shows that the method of in-line determination of polymer concentration corrects for sample size or concentration.

All cited patents and other references are incorporated herein by reference.

What is claimed is:

1. A method for the determination of polymer molecular weight, comprising:

injecting a known volume of an analytical sample comprising a polymer reaction product of a diphenyl carbonate and a dihydric phenol into a flow analysis system comprising an on line flow path through (1) a chromatographic column, (2) a sequential concentration detector, and (3) a sequential waste reservoir, and an off-line split flow path from the cocentration detector to a molar mass detector then to the waste reservior;

effecting a minimally dispersive separation of the analytical sample with the chromatographic column to yield a first high molecular weight fraction in solvent;

determining a polymer concentration in the high molecular weight fraction in solvent using the concentration detector;

separating the high molecular weight fraction in solvent into a diverted high molecular weight fraction and a portion comprising solvent;

discharging the solvent portion directly and without further processing to the waste reservoir;

determining off-line the molar mass using the split flow path molar mass detector on the diverted high molecular weight fraction; and deriving an average molecular weight from the polymer concentration and the molar mass.

2. The method of claim 1, comprising effecting rapid mixing of the diverted high molecular weight fraction prior to determining the molar mass off-line.

3. The method of claim 1, wherein the diverted high molecular weight fraction comprises high molecular weight fraction polycarbonate oligomers and polymers comprising at least two bisphenol A units.

4. The method of claim 1, wherein the polymer comprises an aromatic polycarbonate.

5. The method of claim 1, wherein the dihydric phenol is selected from the group consisting of 2,2-bis-(4-hydroxyphenyl)propane; hydroquinone; resorcinol; 2,2-bis-(4-hydroxyphenyl)pentane; 2,4'-dihydroxydiphenylmethane; bis-(2-hydroxyphenyl)methane; bis-(4-hydroxyphenyl)methane; bis-(4-hydroxy-5-nitrophenyl)methane; 1,1-bis-(4-hydroxyphenyl)ethane; 3,3-bis-(4-hydroxyphenyl)pentane; 2,2'-dihydroxydiphenyl; 2,6-dihydroxynapthylene; bis-(4-hydroxyphenyl)sulfone; 2,2'-dihydroxydiphenylsulfone; 4,4'-dihydroxydiphenylether; 4,4'-dihydroxy-2,5-diethoxydiphenylether; and 1,1-bis(3-methyl-4-hydroxyphenyl)cyclohexane.

6. The method of claim 1, wherein the average molecular weight is a number average molecular weight.

7. The method of claim 1, wherein the solvent is selected from the group consisting of benzene, toluene, xylene, chloroform, tetrahydrofuran, methylenechloride, trichloroethylene, dichloroethane, chlorobenzene, dichlorobenzene, trichlorobenzene, methyl acetate, ethyl acetate, hexafluoroisopropanol, and mixtures comprising at least one of the foregoing solvents.

8. The method of claim 1, wherein the solvent is selected from the group consisting of benzene, toluene, xylene, chloroform, tetrahydrofuran, dichloromethane, and mixtures comprising at least one of the foregoing.

9. The method of claim 1, wherein the average molecular weight is a weight average molecular weight.

10. The method of claim 1, wherein the minimally dispersive separation yields a high molecular weight fraction substantially free of monomers and polymerization catalysts.

11. The method of claim 1, wherein the chromatographic column comprises at least one size exclusion chromatographic column.

12. The method of claim 1, wherein the minimally dispersive separation yields a high molecular weight fraction having a baseline peak width less than about 30 seconds at least one of the molar mass detector or the concentration detector.

13. The method of claim 1, wherein the minimally dispersive separation yields a high molecular weight fraction having a baseline peak width less than about 20 seconds at least one of the molar mass detector or the concentration detector.

14. The method of claim 1, wherein the minimally dispersive separation yields a high molecular weight fraction having a baseline peak width less than about 10 seconds at least one of the molar mass detector or the concentration detector.

15. The method of claim 1, wherein the minimally dispersive separation yields a high molecular weight fraction having a peak width at half height less than about 10 seconds at least one of the moler mass detector or the concentration detector.

16. The method of claim 1, wherein the minimally dispersive separation yields a high molecular weight fraction having a peak width at half height less than about 5 seconds at least one of the molar mass detector or the concentration detector.

17. The method of claim 1, wherein the minimally dispersive separation yields a high molecular weight fraction having a peak width at half height less than about 3 seconds at least one of the molar mass detector or the concentration detector.

18. The method of claim 1, wherein the concentration detector utilizes one or more detection methods selected from the group consisting of infrared absorption spectroscopy, ultraviolet absorption spectroscopy, differential refractive index detection, fluorescence detection, ultrasonic detection, and evaporative light scattering detection.

19. The method of claim 1, wherein the molar mass detector utilizes one or more detection methods selected from the group consisting of the light scattering, low angle light scattering, multiangle light scattering and viscometry.

20. The method of claim 1, wherein the molar mass detector utilizes multiangle light scattering.

21. The method of claim 1, wherein determining the polymer concentration and determining the molar mass are conducted sequentially.

22. The method of claim 1, wherein the total analysis time is not greater than about 3 minutes per sample.

23. The method of claim 1, wherein the total analysis time is not greater then about 1 minute per sample.

24. The method of claim 1, wherein the total analysis time is not greater than about 40 seconds per sample.

25. A method for the determination of polymer molecular weight, comprising:

providing a sample array comprising a plurality of spatially differentiated sites, each site comprising a polymer resin reaction product of a diphenyl carbonate and bisphenol A;

preparing an analytical sample for each spatially differentiated site by dissolving the polymer resin reaction product in a suitable solvent;

injecting a known amount of the analytical sample into a flow analysis system comprising an on-line flow path of sequential chromatographic column, a concentration detector, and a waste reservoir;

effecting a minimally dispersive separation of the analytical sample with the chromatographic column to yield a high molecular weight fraction comprising polycarbonate oligomers and polymers comprising at least two bisphenol A units, said fraction being substantially free of monomers;

determining a polymer concentration in the high molecular weight fraction of the analytical sample using the concentration detector;

diverting a portion of the analytical sample to the split flow path of the molar mass detector and disposing the remainder of the analytical sample to the waste reservoir without further processing; and determining the molar mass in the high molecular weight fraction of the diverted portion of the analytical sample using the molar mass detector; and deriving an average molecular weight for the analytical sample based on the polymer concentration and the molar mass.

26. The method of claim 25, wherein preparing an analytical sample for each spatially differentiated site, injecting a known amount of the analytical sample, effecting a minimally dispersive separation of the analytical sample, determining the polymer concentration in the high molecular weight fraction of the analytical sample, determining the molar mass in the high molecular weight fraction of the analytical sample, and deriving an average molecular weight for the analytical sample are conducted without human intervention.

27. The method of claim 25, wherein the minimally dispersive separation yields a high molecular weight fraction having a baseline peak width less than about 30 seconds.

28. The method of claim 25, wherein the minimally dispersive separation yields a high molecular weight fraction having a baseline peak width less than about 20 seconds.

29. The method of claim 25, wherein the minimally dispersive separation yields a high molecular weight fraction having a baseline peak width less than about 10 seconds.

30. The method of claim 25, wherein the minimally dispersive separation yields a high molecular weight fraction having a peak width at half height less than about 10 seconds.

31. The method of claim 25, wherein the minimally dispersive separation yields a high molecular weight fraction having a peak width at half height less than about 5 seconds.

32. The method of claim 25, wherein the minimally dispersive separation yields a high molecular weight fraction having a peak width at half height less than about 3 seconds.

33. The method of claim 25, wherein the diverted high molecular weight fraction comprises high molecular weight fraction polycarbonate oligomers and polymers comprising at least two bisphenol A units.

34. The method of claim 25, comprising effecting rapid mixing of the diverted high molecular weight fraction prior to determining the molar mass off-line.

* * * * *